United States Patent
Shew

(10) Patent No.: US 12,285,588 B1
(45) Date of Patent: Apr. 29, 2025

(54) INTRAVENOUS POLE ORGANIZER FOR MEDICAL TUBING AND/OR WIRING

(71) Applicant: Sheryl J. Shew, Longview, WA (US)

(72) Inventor: Sheryl J. Shew, Longview, WA (US)

( * ) Notice: Subject to any disclaimer, the term of this patent is extended or adjusted under 35 U.S.C. 154(b) by 0 days.

(21) Appl. No.: 18/793,267

(22) Filed: Aug. 2, 2024

(51) Int. Cl.
*A61M 5/14* (2006.01)

(52) U.S. Cl.
CPC ..... *A61M 5/1418* (2013.01); *A61M 2209/082* (2013.01); *A61M 2209/084* (2013.01)

(58) Field of Classification Search
CPC .......... A61M 5/1418; A61M 2209/082; A61M 2209/084
See application file for complete search history.

(56) References Cited

U.S. PATENT DOCUMENTS

| | | | | |
|---|---|---|---|---|
| 4,953,819 | A * | 9/1990 | Davis ................... | A61M 5/1415 248/230.8 |
| 5,056,747 | A * | 10/1991 | Kireta ..................... | F21S 4/20 248/74.2 |
| 9,198,727 | B1 * | 12/2015 | Samuels ............... | A61F 15/001 |
| 11,400,208 | B2 * | 8/2022 | Millar .................. | A61M 5/1417 |
| 11,471,344 | B1 * | 10/2022 | Turnbow ................. | A61G 5/10 |
| 2001/0049504 | A1 * | 12/2001 | Gautsche ............... | A61B 46/23 604/179 |
| 2002/0096608 | A1 * | 7/2002 | Cedarberg, III .... | A61M 5/1418 248/68.1 |
| 2007/0282272 | A1 * | 12/2007 | Bannon ................ | A61M 5/1418 604/174 |
| 2008/0011907 | A1 * | 1/2008 | Jacobsma ............. | F16L 33/035 248/62 |
| 2008/0086090 | A1 | 4/2008 | Raines | |
| 2008/0097333 | A1 * | 4/2008 | Henning ............. | A61M 5/1418 604/174 |
| 2010/0040307 | A1 * | 2/2010 | Lien ...................... | A45F 5/1046 383/12 |
| 2012/0016310 | A1 * | 1/2012 | Holliday ............... | A61M 25/02 604/174 |
| 2014/0306070 | A1 * | 10/2014 | Hartsock ............. | A61M 5/1418 248/68.1 |
| 2017/0114988 | A1 * | 4/2017 | Andretta-Pulera ....... | F21S 4/26 |
| 2018/0240380 | A1 * | 8/2018 | Horgash .............. | G09F 15/0037 |
| 2018/0338810 | A1 * | 11/2018 | Lampropoulos ....... | A61B 46/40 |

FOREIGN PATENT DOCUMENTS

| | | | |
|---|---|---|---|
| KR | 102237694 B1 * | 4/2021 | |
| WO | WO-2014190424 A1 * | 12/2014 | ............ A61M 25/02 |

* cited by examiner

*Primary Examiner* — Kimberly T Wood
(74) *Attorney, Agent, or Firm* — FORTEM IP LLP

(57) ABSTRACT

Systems and methods for organizing medical tubing and/or wiring are disclosed herein. According to some embodiments, the present technology includes an organizer including a tubular member configured to be removably coupled to an intravenous (IV) pole in a vertical orientation. The tubular member can include a longitudinal axis, a lumen extending along the longitudinal axis, and a longitudinal slit connected to the lumen. The tubular member can be configured to separate at the longitudinal slit to insert and remove the IV pole from the lumen. The organizer can further include a plurality of holders coupled to the tubular member. The plurality of holders can include a first end, a second end opposite the first end, and a curved receiving region between the first and second ends. The curved receiving region can be configured to support tubing or wiring of a medical device coupled to the IV pole.

30 Claims, 10 Drawing Sheets

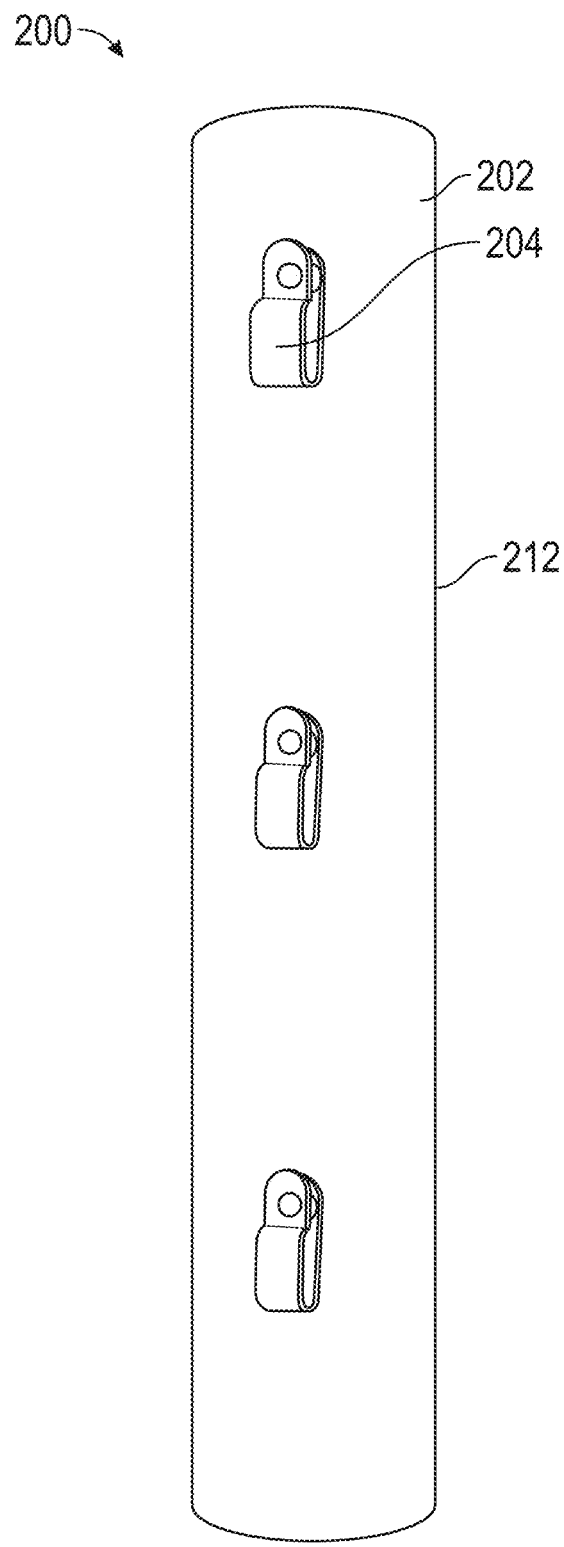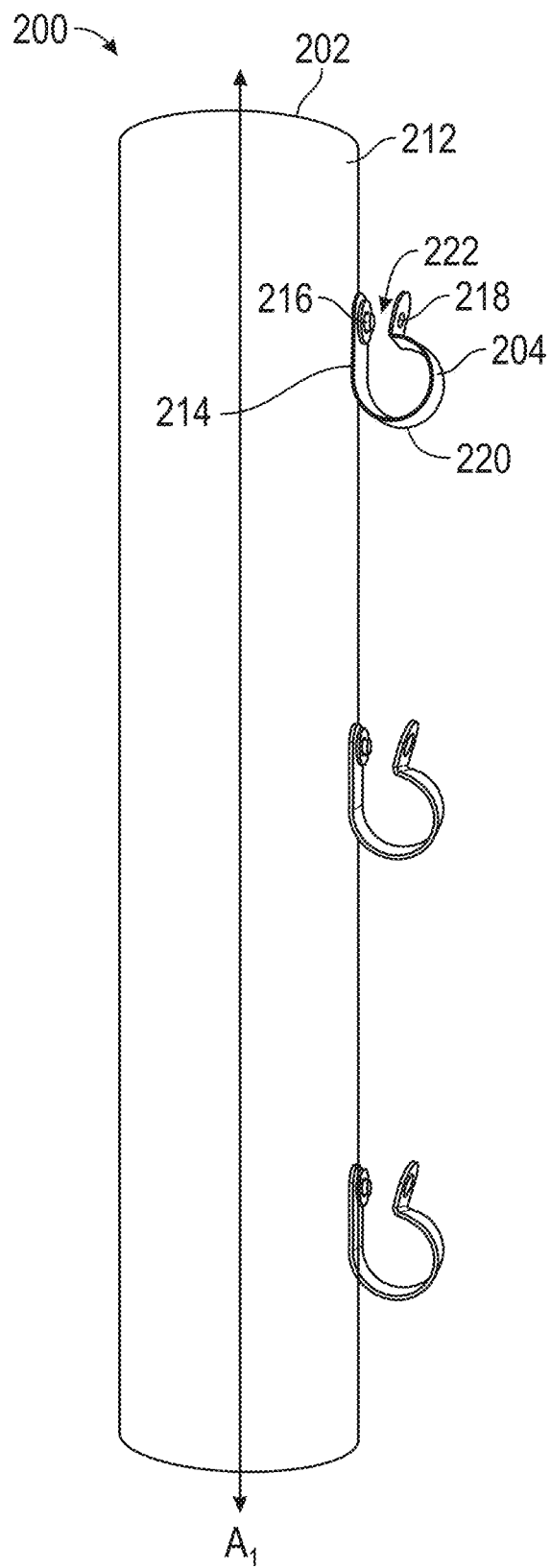
FIG. 2D
FIG. 2E

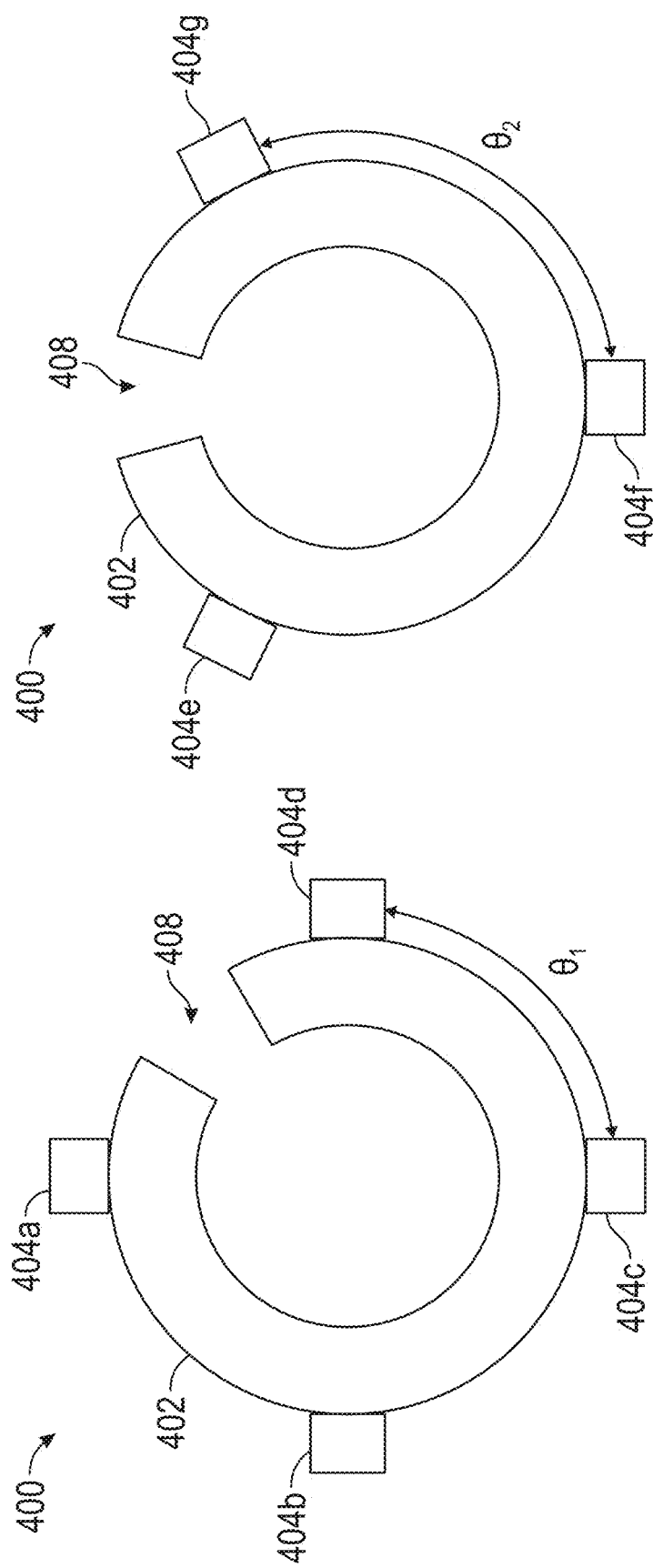

INTRAVENOUS POLE ORGANIZER FOR MEDICAL TUBING AND/OR WIRING

TECHNICAL FIELD

The present technology generally relates to an intravenous pole organizer for medical tubing and/or wiring.

BACKGROUND

Medical care can involve the administration of intravenous (IV) fluids to a patient to support recovery. IV fluids can be delivered through medical tubing from an IV source (e.g., an IV bag) directly to one of the patient's veins. Oftentimes, the IV source is mounted on an IV pole, and the IV pole can support other medical devices having additional wiring and/or tubing. In some cases, the medical tubing from the IV source can become entangled with other equipment in the patient environment, such as the additional wiring and/or tubing, patient beds, chairs, monitors, other electronic devices, etc. This can create a fall hazard, lead to incorrectly administered medication, and/or disrupt bedside care. Further, contact between the medical tubing and unsanitary surfaces can increase the risk of contamination of the IV fluids. Thus, there remains a need for improved medical tubing and/or wiring organization.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

FIG. 2D is a front view of the organizer of FIG. 2A, in accordance with embodiments of the present technology.

FIG. 2E is a side view of the organizer of FIG. 2A, in accordance with embodiments of the present technology.

FIGS. 4A-4D illustrate an organizer with a spiral holder configuration, in accordance with embodiments of the present technology.

DETAILED DESCRIPTION

Figure 1:
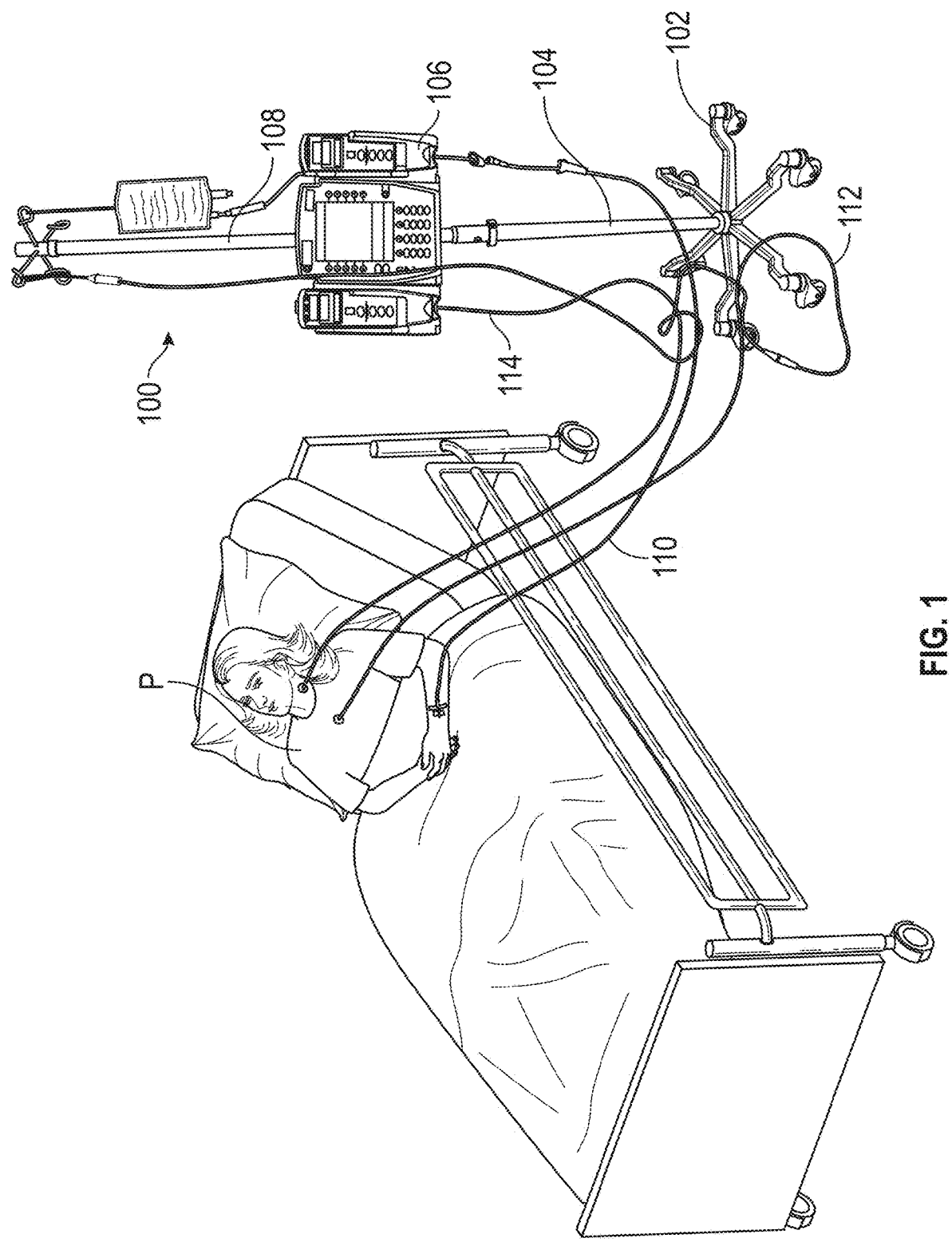
FIG. 1 illustrates an example support device.

The present technology provides devices including features that organize and support medical tubing and/or wiring in a hospital room or other inpatient or outpatient setting. In some embodiments, for example, an organizer includes a tubular member (e.g., a foam tube) configured to be removably coupled to an intravenous (IV) pole in a vertical orientation. The tubular member can include a longitudinal axis, a lumen extending along the longitudinal axis, and a longitudinal slit connected to the lumen. The tubular member can be configured to separate (e.g., split) at the longitudinal slit to insert and remove the IV pole from the lumen. The organizer can also include a plurality of holders (e.g., hooks) coupled to the tubular member. Each of the holders can include a first end pivotally coupled to the tubular member, a second opposite the first end, and a curved receiving region between the first end and the second end. The curved receiving region can be configured to support tubing and/or wiring of a medical device coupled to the IV pole (e.g., an IV bag or pump and/or a patient monitor). Further, the first end and the second end can be separated by a gap for inserting and removing the tubing and/or wiring from the curved receiving region, and the gap can be vertically above the curved receiving region when the tubular member is coupled to the IV pole in the vertical orientation.

Also provided herein are methods for organizing and supporting medical tubing and/or wiring. The method can include positioning a medical organizer on an IV pole in a vertical orientation. The medical organizer can include a tubular member (e.g., a foam tube) having a longitudinal axis, a lumen extending along the longitudinal axis, and a longitudinal slit connected to the lumen. The IV pole can be inserted into the lumen of the tubular member via the longitudinal slit. The medical organizer can further include a plurality of holders (e.g., hooks) coupled to the tubular member. Each of the holders can include a first end that is pivotally coupled to the tubular member, a second end opposite the first end, and a curved receiving region between the first end and the second end. Further, the first end and the second end can be separated by a gap that is vertically above the curved receiving region when the tubular member is coupled to the IV pole in the vertical orientation. The method can further include inserting medical tubing and/or wiring from a medical device (e.g., an IV pump or display) coupled to the IV pole through the gap and into the curved receiving region of one or more of the holders. The method can further include removing the medical organizer from the IV pole via the longitudinal slit in the tubular member, optionally while the medical tubing and/or wiring is retained in the one or more holders. The method can further include positioning the medical organizer in the vertical orientation on a support device different from the IV pole (e.g., a walker).

The organizers and methods described herein can provide many advantages. Since the organizers can include a plurality of holders configured to receive medical tubing and/or wiring, the positioning and management of medical tubing and/or wiring can be improved. For instance, the medical tubing and/or wiring can be supported at multiple points on the organizer in an orderly and secure manner. This can reduce the risk of entanglement, catheter displacement (e.g., IV dislodgement), and/or tripping. Further, the organizers can help prevent the medical tubing and/or wiring from contacting unsanitary surfaces, such as hospital floors or walls, thereby decreasing the risk of contamination. The organizer can also provide an appearance of cleanliness, which may improve patient comfort and confidence. Moreover, the organizer can be easily and safely removed and repositioned from one support device (e.g., an IV pole) to another (e.g., a patient's walker), thereby allowing for improved patient mobility during recovery, faster patient transfer between different locations (e.g., from a hospital room to an operating room), and more flexible bedside care. Additionally, in some embodiments, the organizer is a vertically-oriented organizer, and the medical tubing and/or wiring can rest on the plurality of holders via gravity such that they are easily repositioned while being sufficiently retained.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

As used herein, the terms "vertical," "lateral," "upper," "lower," "left," "right," etc., can refer to relative directions or positions of features of the embodiments disclosed herein in view of the orientation shown in the Figures. For example, "upper" or "uppermost" can refer to a feature positioned closer to the top of a page than another feature. These terms, however, should be construed broadly to include embodiments having other orientations, such as inverted or inclined orientations where top/bottom, over/under, above/below, up/down, and left/right can be interchanged depending on the orientation.

Organizers of the present technology can include features that provide support for medical tubing and/or wiring. In some embodiments, for example, an organizer includes a tubular member (e.g., a foam tube), and a plurality of holders (e.g., hooks) coupled to the tubular member. Medical tubing and/or wiring can be supported by the plurality of holders, thus avoiding entanglement, tripping hazards, and/or contact with unsanitary surfaces. Moreover, the plurality of holders can retain the medical tubing and/or wiring while the organizer is repositioned on a support device (e.g., an IV pole), such as by sliding and/or rotating the organizer along the support device, thereby allowing for rapid and easy adjustments to the organizer (e.g., to accommodate repositioning of the patient and/or support device, addition or removal of medical devices from the support device) while keeping the medical tubing and/or wiring supported and organized. Moreover, the organizer can be rapidly removed from the support device and positioned on a different support device (e.g., a patient's walker), thereby allowing for improved patient mobility during recovery, faster patient transfer, and/or more flexible bedside care. In some embodiments, the plurality of holders are each pivotally coupled to the tubular member, such that the plurality of holders can rotate relative to the tubular member to support the medical tubing and/or wiring in a variety of positions and orientations, thus allowing for flexibility in the organization of the medical tubing and/or wiring, as well as reducing the likelihood of the medical tubing and/or wiring becoming inadvertently dislodged from the holders when the patient and/or support device are moved.

FIG. 1 illustrates an example of a support device 100 that may benefit from the use of an organizer described herein. The support device 100 can be an IV pole including a base 102 and an elongate vertical body 104. The support device 100 can be configured to carry one or more medical devices 106 (e.g., IV bags, IV pumps, displays, diagnostic equipment, sensing equipment, therapeutic equipment, electronic communication devices, etc.). For instance, as shown in FIG. 1, a medical device 106, such as an IV pump, can be attached to an upper or middle section 108 of the vertical body 104. In some situations, the medical devices 106 carried by the support device 100 include medical tubing and/or wiring connecting the medical devices 106 to the patient and/or to other locations (e.g., power outlets, other medical devices). In the example of FIG. 1, the medical device 106 includes a first plurality of medical tubes 110 extending toward a patient P on a patient bed. However, as depicted in FIG. 1, the support device 100 does not have components for supporting and/or organizing the medical tubes 110. As a result, a portion of the medical tubes 110 between the medical device 106 and the patient P may rest on the floor of the patient environment, where they pose a risk of tripping, entanglement, and/or contamination.

Further, the medical tubes 110 may be prone to becoming entangled with additional tubing and/or wiring from other devices on or proximate to the support device 100. For instance, in the example of FIG. 1, additional medical tubes 112 and/or medical wiring 114 can extend from elsewhere in the patient's room toward the patient P on the patient bed. For instance, the medical tubes 112 and/or medical wiring 114 can extend from a dialysis machine, pulse oximeter, patient monitor, etc. In some examples, the medical tubes 110, medical tubes 112, and/or medical wiring 114 can become entangled with each other.

FIG. 1 may be representative of the disorganization of medical tubing and/or wiring that occurs in many hospital rooms, where medical tubing is draped from a support device (e.g., an IV pole) directly to a patient's bed, without any intermediary support. In such cases, the medical tubing can provide an obstruction to the patient and/or medical professionals, may become entangled with other equipment, and/or may be contaminated via contact with unsanitary surfaces. The general disorganization may also produce an unhygienic appearance. Further, the disorganization may make it difficult for medical professionals to identify the appropriate tubing and/or wiring for a particular operation (e.g., connecting and/or disconnecting medical devices). Additionally, it may be cumbersome for the patient to move around the hospital room (such as to use the bathroom), as the medical tubing would need to be disentangled and removed from the support device prior to patient movement.

In some embodiments, the present technology includes an organizer for medical tubing and/or wiring for use with a variety of support devices in a patient room or other inpatient or outpatient setting. The organizer can include a tubular member and a plurality of holders coupled to the tubular member. The organizer can be placed in a vertical orientation on a support device (e.g., an IV pole), and the plurality of holders can be configured to support medical tubing and/or wiring of a medical device coupled to the support device.

Figure 2A:
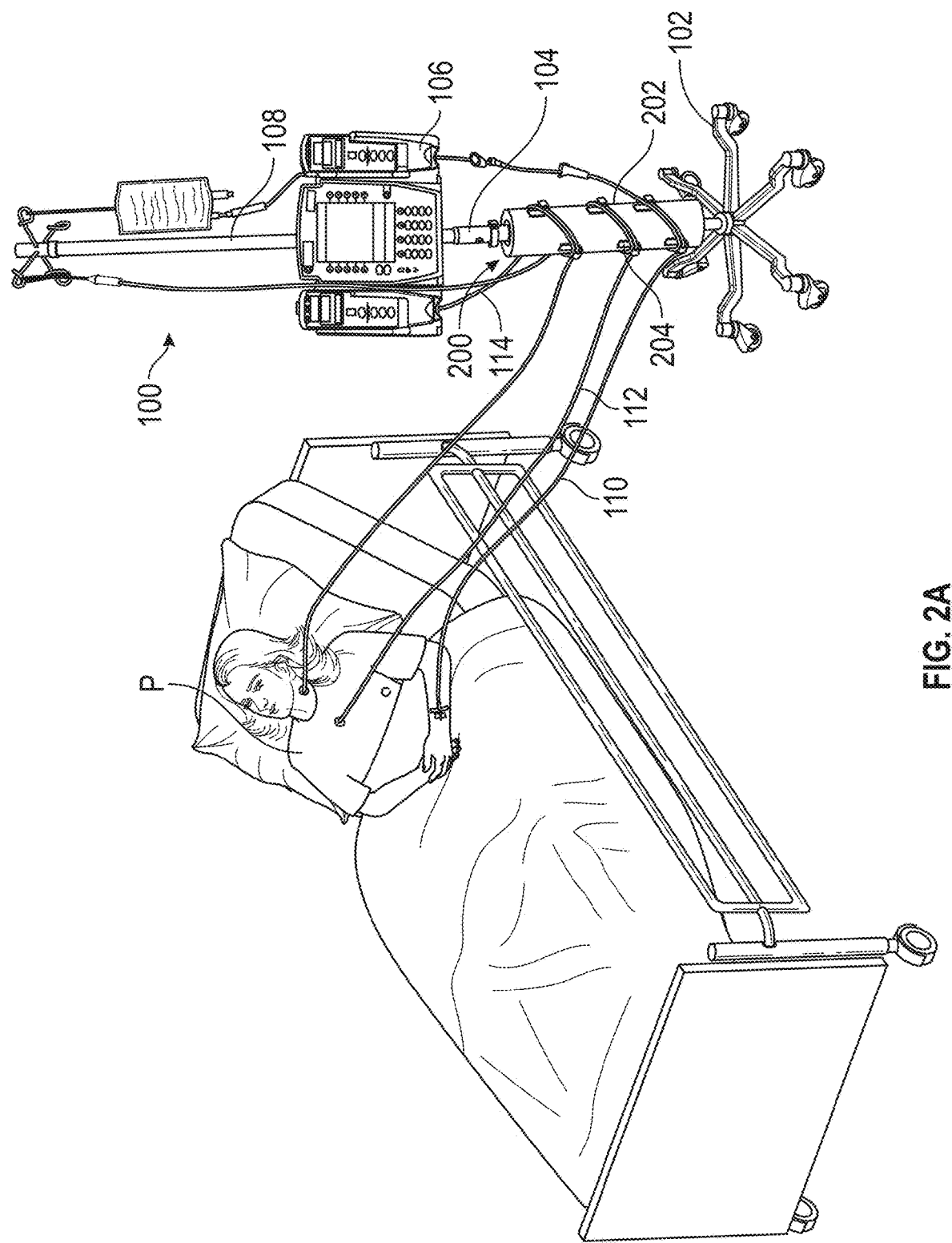
FIG. 2A illustrates an organizer positioned on a support device, in accordance with embodiments of the present technology.
Figure 2B:
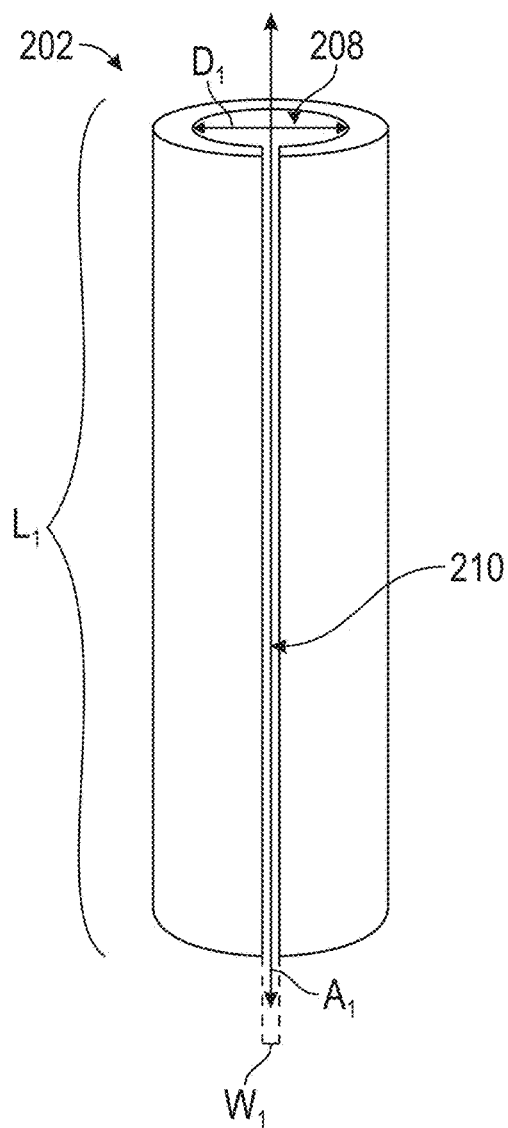
FIG. 2B is a rear view of a tubular member of the organizer of FIG. 2A, in accordance with embodiments of the present technology.
Figure 2C:
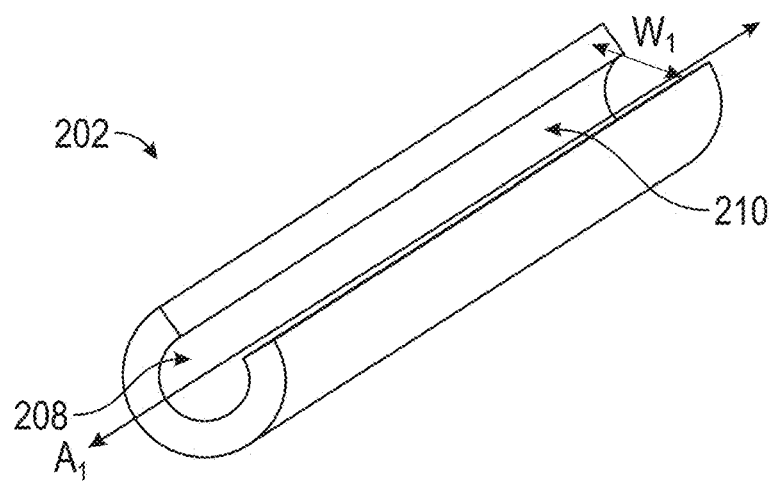
FIG. 2C is a perspective view of the tubular member of the organizer of FIG. 2A, in accordance with embodiments of the present technology.

FIGS. 2A-2E illustrate an example of an organizer 200 including a tubular member 202 and a plurality of holders 204, in accordance with embodiments of the present technology. Specifically, FIG. 2A illustrates the organizer 200 positioned on a support device 100, FIG. 2B is a rear view of the tubular member 202 of the organizer 200, FIG. 2C is a perspective view of the tubular member 202 of the organizer 200, FIG. 2D is a front view of the organizer 200, and FIG. 2E is a side view of the organizer 200.

Referring first to FIG. 2A, the organizer 200 can be used to support medical tubing and/or wiring 110-114 from one or more medical devices 106 on or proximate to the support devices 100 in a patient environment (e.g., a hospital room).

For instance, the organizer 200 can be positioned on the support device 100 (e.g., on a section of the elongate vertical body 104 of the support device 100 above the base 102). In some embodiments, the support device 100 is an IV pole, as depicted in FIG. 2A. Alternatively, the support device 100 can be or include a patient walker, wheelchair, chair, bed, shower accessory, etc. Moreover, the organizer 200 can be configured to be removably coupled to the support device 100 such that the organizer 200 can be positioned on and/or removed from the support device 100, and optionally, positioned on and/or removed from an additional support device different from the support device 100. The medical devices 106 can include IV bags, IV pumps, displays, diagnostic equipment, sensing equipment (e.g., pulse oximeters, patient monitors), therapeutic equipment (e.g., dialysis machines), electronic communication devices, etc.

Referring next to FIGS. 2A-2E together, the organizer 200 can be configured to be removably coupled to the support device 100 via the tubular member 202 of the organizer 200. For instance, the tubular member 202 can have suitable dimensions such that the tubular member 202 can be configured to at least partially surround a portion of the support device 100. In some embodiments, the tubular member 202 has an inner diameter Di (FIG. 2B) that is greater than or equal to an outer diameter of the support device 100 when the organizer 200 is coupled to the support device 100. The inner diameter Di of the tubular member 202 can be, for example, within a range from 5 mm to 15 mm, 15 mm to 30 mm, 30 mm to 45 mm, 45 mm to 60 mm, or 60 mm to 75 mm. Further, the tubular member 202 can have a wall thickness of at least 5 mm, 10 mm, 20 mm, 50 mm, 100 mm, etc. In some embodiments, the wall of the tubular member 202 can provide a platform for attaching the plurality of holders 204, as will be discussed further herein. Accordingly, the wall can be sufficiently thick to accommodate and support the holders 204, while remaining sufficiently thin to avoid adding excessive weight to the organizer 200.

In some embodiments, the tubular member 202 is configured to extend along a length of the support device 100 when the organizer 200 is coupled to the support device 100. For instance, the tubular member 202 can have an axial length Li (FIG. 2B) of at least 10 cm, 20 cm, 50 cm, 1 m, 1.5 m, etc. In some embodiments, the organizer 200 can be made of a material that can be cut to a desired length. For example, the tubular member 202 can be cut from its upper and/or lower ends to reduce the length Li of the tubular member 202 to fit onto the support device 100. Alternatively or in combination, the tubular member 202 can be cut into multiple discrete sections that are each configured to be positioned and retained on the support device 206. For instance, the tubular member 202 may be cut into tubular sections each having an axial length of no greater than 50 cm, 20 cm, 10 cm, etc. Each of the tubular sections can act as standalone tubular members, and the discussion of tubular members herein can also apply to each of the individual tubular sections.

The tubular member 202 of the organizer 200 can be configured to be removably coupled to the support device 100 in a vertical orientation. In some embodiments, as shown in FIGS. 2B and 2C, the tubular member 202 includes a lumen 208 extending along a longitudinal axis $A_1$. The lumen 208 can be sized and/or shaped to receive the portion of the support device 100 to which the organizer 200 is coupled. For instance, if the portion of the support device 100 is cylindrical, then the lumen 208 can be cylindrical; if the portion of the support device 100 is rectangular, then the lumen 208 can be rectangular; if the support device 100 has a curved body, then the lumen 208 can have a corresponding and/or accommodating curvature; etc. In some embodiments, the entire lumen 208 has a matching and/or complementary geometry to the portion of the support device 100, while in other embodiments, the lumen 208 may instead include only some regions that are matching and/or complementary. In some embodiments, for example, the lumen 208 may not be entirely flush with the portion of the support device 100 and only contacts the support device 100 at select regions.

In general, the longitudinal axis $A_1$ can be coaxial with and/or parallel to the longitudinal axis of the support device 100 when the organizer 200 is coupled to the support device 100. For instance, when the support device 100 is an IV pole having a vertically-oriented longitudinal axis, the longitudinal axis $A_1$ can also be vertical when the organizer 200 is coupled to the IV pole. In some embodiments, the vertical orientation of the longitudinal axis $A_1$ can improve the convenience of inserting and removing medical tubing and/or wiring from the organizer 200, as will be discussed further herein.

In some embodiments, the tubular member 202 is configured to be coupled to the support device 100 without requiring straps, buckles, latches, or other fasteners that are coupled to the tubular member 202. Instead, the tubular member 202 itself can provide sufficient coupling forces for securing the organizer 200 to the support device 100. For example, the tubular member 202 can further include a longitudinal slit 210 connected to the lumen 208. The longitudinal slit 210 may be parallel to the longitudinal axis $A_1$ and can extend along the entire length Li of the tubular member 202. In some embodiments, the tubular member 202 is configured to separate at the longitudinal slit 210 to insert and remove the support device 100 from the lumen 208. For instance, prior to use, the tubular member 202 can be in a closed configuration (FIG. 2B) in which the longitudinal slit 210 has a relatively small slit width $W_1$ (e.g., no more than 20 mm, 10 mm, 5 mm, 2 mm, or 1 mm). To couple the tubular member 202 to the support device 100, an external force can be applied to the tubular member 202 to place the tubular member 202 in an open configuration (FIG. 2C) in which the tubular member 202 is separated at the longitudinal slit 210, thereby widening the slit width $W_1$ to an increased width, e.g., at least 10 mm, 20 mm, 50 mm, etc. The increased width can be sufficiently large to allow the portion of the support device 100 to pass through the longitudinal slit 210 and into the lumen 208. Subsequently, the external force on the tubular member 202 can be released to allow the tubular member 202 to revert back toward the closed configuration, thereby narrowing the slit width $W_1$ so the support device 100 is retained within the lumen 208 of the tubular member 202.

In some embodiments, the tubular member 202 is configured to apply compressive forces to the support device 100 to secure the tubular member 202 to the support device 100 after placement. The compressive forces applied by the tubular member 202 can arise from intrinsic elastic forces of the tubular member 202. For instance, the tubular member 202 can be composed of one or more elastic materials (e.g., a polymeric material such as polyethylene) that resists deformation. In some embodiments, prior to use, the tubular member 202 is in a resting configuration (e.g., the closed configuration of FIG. 2B) in which the inner diameter Di of the tubular member 202 is smaller than the outer diameter of the support device 100. When the tubular member 202 is coupled to the support device 100, the tubular member 202 can be stretched so that the inner diameter Di of the tubular member 202 is enlarged to match and/or exceed the outer diameter of the support device 100. The resistance of the elastic material of the tubular member 202 to the stretching can exert compressive forces against the support device 100 to retain the tubular member 202 on the support device 100.

In some embodiments, the tubular member 202 can be repositioned on the support device 100 without having to remove the tubular member 202 from the support device 100. For instance, the tubular member 202 can be moved from a first vertical position on the support device 100 to a second vertical position on the support device 100 (e.g., by sliding the tubular member 202 along the support device 100), and the compressive forces exerted by the tubular member 202 can retain the tubular member 202 in the second vertical position. Alternatively, or in combination, the tubular member 202 can be rotated from a first orientation to a second orientation on the support device (e.g., by sliding the tubular member 202 around the support device 100), and the compressive forces can retain the tubular member 202 in a set vertical position on the support device 100 during the rotation.

The tubular member 202 can be configured to apply frictional forces to the support device 100 to prevent unintentional slippage of the organizer 200 on the support device 100. The frictional forces may be sufficiently high to prevent unintentional movements while being sufficiently low to allow intentional movements, e.g., as discussed herein with respect to repositioning the organizer 200. In some embodiments, the frictional forces arise from a rough and/or uneven inner surface of the tubular member 202. Alternatively or in combination, the tubular member 202 can include one or more materials having a high frictional coefficient, such as a rubber.

Alternatively or in combination, the tubular member 202 can be configured to be coupled to the support device 100 with straps, buckles, latches, and/or other fasteners. For instance, the tubular member 202 may include a plurality of insertion slots (not depicted) for inserting a coupling device. The insertion slots can be positioned adjacent to the longitudinal slit 210. In some embodiments, a coupling device can be inserted into the insertion slots, and the coupling device can be configured to decrease the width of the longitudinal slit 210. For instance, the coupling device can be a strap that is coupled to opposing insertion slots adjacent to the longitudinal slit 210. The strap can be tightened to decrease the width of the longitudinal slit 210. Alternatively or in combination, the coupling device can include a buckle coupled to opposing insertion slots adjacent to the longitudinal slit 210, and the buckle can be fastened to decrease the width of the longitudinal slit 210. Alternatively or in combination, one or more bridge and/or hose clamps can be positioned surrounding the tubular member 202, and the bridge and/or hose clamps can be tightened to decrease the width of the longitudinal slit 210.

The tubular member 202 can be made out of any material that is sufficiently flexible and/or deformable to allow the tubular member 202 to be removably coupled to the support device 206 as described above. In some embodiments, the tubular member 202 includes a foam material. For instance, the tubular member 202 can include a polymeric foam (e.g., polyurethane foam, polyethylene foam, neoprene foam, latex foam, polypropylene foam). The foam material can be a closed-cell foam, reticulated foam, etc. Alternatively or in combination, the tubular member 202 can include one or more non-foam materials such as metals (e.g., stainless steel, aluminum, zinc, copper, various shape memory metals), polymers (e.g., rubber, nylon, silicone, plastics, PTFE), and/or ceramics. The tubular member 202 can additionally or alternatively include one or more antimicrobial materials. For instance, the tubular member can include or be coated with silver, copper, gold, gallium, zinc oxide, magnesium oxide, titanium dioxide, organosilane, etc. In some embodiments, the tubular member 202 is composed of an antimicrobial foam material, e.g., a polymeric foam that includes or is coated with one or more antimicrobial materials.

Turning now to FIGS. 2D and 2E, the plurality of holders 204 can be coupled to the tubular member 202, e.g., to the external surface 212 of the tubular member 202. The holders 204 can be hooks, clasps, clips, or other similar fasteners for removably coupling to and supporting medical tubing and/or wiring. In the illustrated embodiment, for example, the holders 204 are curved hooks having a first end 214, a second end 218, and a receiving region 220 extending between the first end 214 and the second end 218. The first end 214 and the second end 218 can be separated by a gap 222 to allow medical tubing and/or wiring to be inserted into and removed from the receiving region 220 via the gap 222.

The holders 204 can be coupled to the tubular member 202 using any suitable technique. For instance, the first end 214 of each of the holders 204 can be coupled to the external surface 212 of the tubular member 202. In some embodiments, the first end 214 is coupled to the tubular member 202 via a fastener 216 (e.g., a screw) extending at least partially through the wall of the tubular member 202 Alternatively or in combination, the first end 214 can be coupled to the tubular member 202 using one or more of adhesives, bonding, straps, etc.

In some embodiments, some or all of the holders 204 are movably coupled to the tubular member 202, e.g., the holders 204 may translate and/or rotate (e.g., pivot) relative to the tubular member 202. In some embodiments, the first end 214 of the holder 204 can be pivotally coupled to the tubular member 202 such that the holder 204 can rotate about the first end 214, e.g., in response to movement of the patient, the medical tubing and/or wiring within the holder 204, the organizer 200, and/or the support device 100. For instance, in response to a tipping motion of the tubular member 202, the holder 204 can rotate (e.g., via gravity) to support the medical tubing and/or wiring. Alternatively or in combination, the pivotal coupling of the holder 204 to the tubular member 202 may allow for manual rotation of the holder 204. This may be useful, for example, to accommodate various tubing and/or wiring geometries. In other embodiments, however, some or all of the holders 204 can be coupled to the tubular member 202 in a fixed position and/or orientation.

The second end 218 of the holder 204 can be a free end that is not connected to the tubular member 202, thereby forming the gap 222 between the first end 214 and the second end 218. The gap 222 can be sufficiently large to allow for convenient insertion and removal of the medical tubing and/or wiring into and from the receiving region 220. At the same time, the gap 222 can be sufficiently small to prevent the tubing and/or wiring from becoming inadvertently dislodged from the receiving region 220. For instance, the gap 222 can have a size within a range from 5 mm to 10 mm, 10 mm to 15 mm, or 15 mm to 20 mm.

The receiving region 220 can be positioned below the first end 214 and second end 218, thereby defining a space within the holder 204 for receiving and retaining medical tubing and/or wiring. In some embodiments, the gap 222 is vertically above the receiving region 220 when the tubular member 202 is coupled to the support device 206 in the vertical orientation. The vertical positioning of the gap 222 relative to the receiving region 220 can allow gravity to facilitate retention of the tubing and/or wiring within the holder 204.

The organizer 200 can include any suitable number of holders 204, such as one, two, three, four, five, 10, 15, 20, 25, or more holders 204. The holders 204 provided herein can include a variety of geometries for providing support to medical tubing and/or wiring in a patient environment. For instance, each component of the holder 204 (e.g., the first end 214, second end 218, receiving region 220, and/or gap 222) can be independently modified and/or varied to produce a differently shaped holder 204. Although FIGS. 2A-2E illustrate holders 204 having a curved shape (e.g., C-shaped or U-shaped), in other embodiments, some or all of the holders 204 can have a different shape, such as a square shape, rectangular shape, curvilinear shape, etc.

Figures 3A, 3B, 3C:
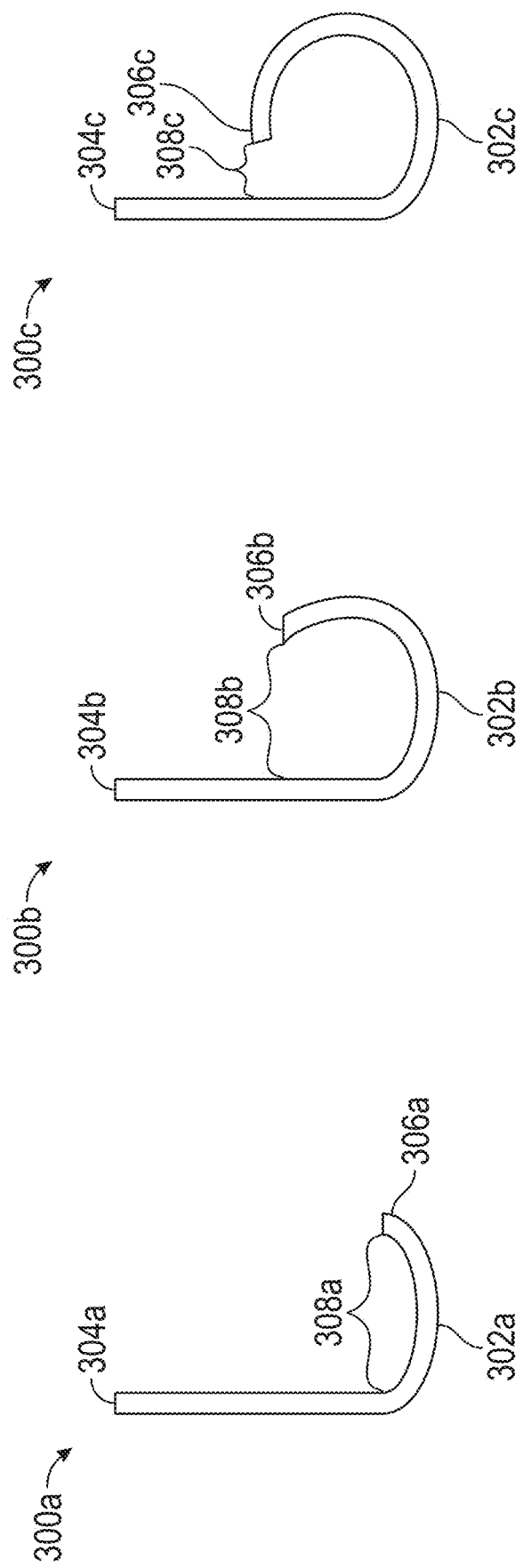
FIGS. 3A-3C illustrate example holders of an organizer, in accordance with embodiments of the present technology.

FIGS. 3A-3C illustrate example holders 300a-300c suitable for use with an organizer in accordance with embodiments of the present technology. The holders 300a-300c can be generally similar to the holders 204 of the organizer 200 of FIGS. 2A-2E, except as described below.

FIG. 3A is a side view of a first holder 300a configured in accordance with embodiments of the present technology. The first holder 300a can include a receiving region 302a extending between a first end 304a and a second end 306a. The first end 304a can be coupled to a tubular member of an organizer and the second end 306a can be a free end that is spaced apart from the first end 304a to define a gap 308a. In the illustrated embodiment, the receiving region 302a can have a low degree of curvature such that the first holder 300a has a relatively large gap 308a. For example, the arc angle of the receiving region 302a (e.g., as measured between the end points of the curved portion of the receiving region 302a) can be less than or equal to 90°, 80°, 70°, 60°, 50°, 45°, 40°, 30°, 20°, or 10°. In some embodiments, the relatively large gap 308a of the holder 300a can allow the holder 300a to receive and support tubing and/or wiring with larger diameters. Additionally, the relatively large gap 308a may provide for easier insertion and/or removal of the tubing and/or wiring.

FIG. 3B is a side view of a second holder 300b configured in accordance with embodiments of the present technology. The second holder 300b can include a receiving region 302b extending between a first end 304b and a second end 306b. The first end 304b can be coupled to a tubular member of an organizer and the second end 306b can be a free end that is spaced apart from the first end 304b to define a gap 308b. In the illustrated embodiment, the receiving region 302b can have an intermediate degree of curvature such that the second holder 300b has an intermediate-sized gap 308b. For example, the arc angle of the receiving region 302b (e.g., as measured between the end points of the curved portion of the receiving region 302b) can be within a range from 90° to 180°, 900 to 150°, 90° to 120°, 1200 to 180°, 120° to 150°, or 150° to 180°. The gap 308b may be useful for allowing the insertion and/or removal of larger amounts of tubing and/or wiring with reduced risk of dislodgement.

FIG. 3C is a side view of a third holder 300c configured in accordance with embodiments of the present technology. The third holder 300c can include a receiving region 302c extending between a first end 304c and a second end 306c. The first end 304c can be coupled to a tubular member of an organizer and the second end 306c can be a free end that is spaced apart from the first end 304c to define a gap 308c. In the illustrated embodiment, the receiving region 302c can have a high degree of curvature such that the third holder 300c has a relatively small gap 308c. For example, the arc angle of the receiving region 302c (e.g., as measured between the end points of the curved portion of the receiving region 302c) can be at least 180°, 225°, 270°, or 315°. The relatively small gap 308c may provide more secure retention of tubing and/or wiring within the third holder 300c.

Figure 4A:
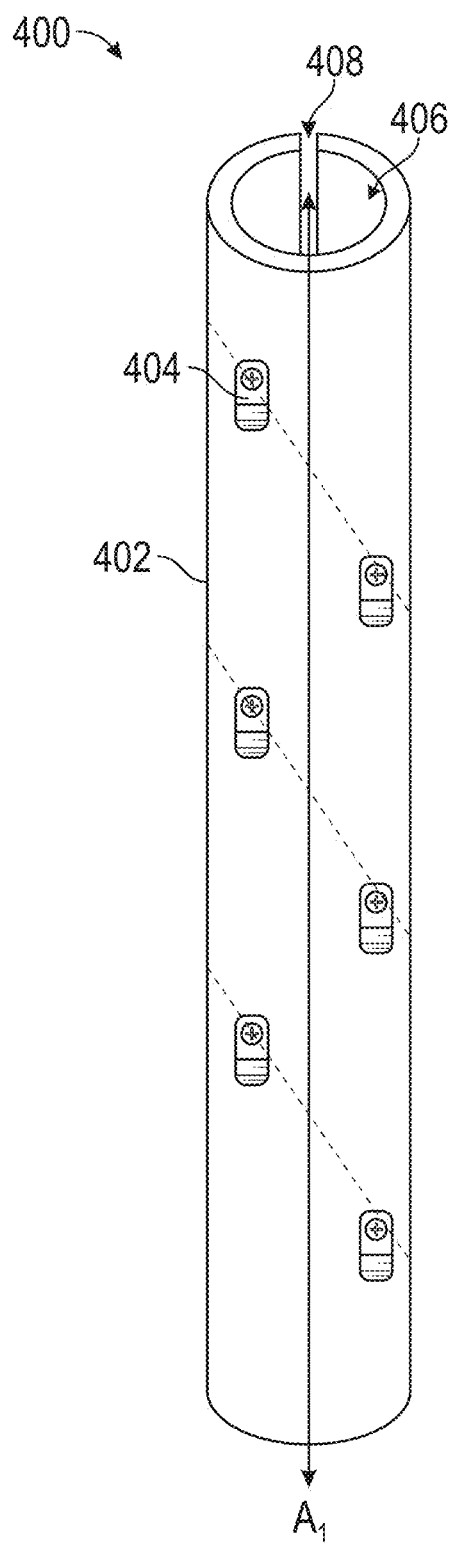
Figure 4B:
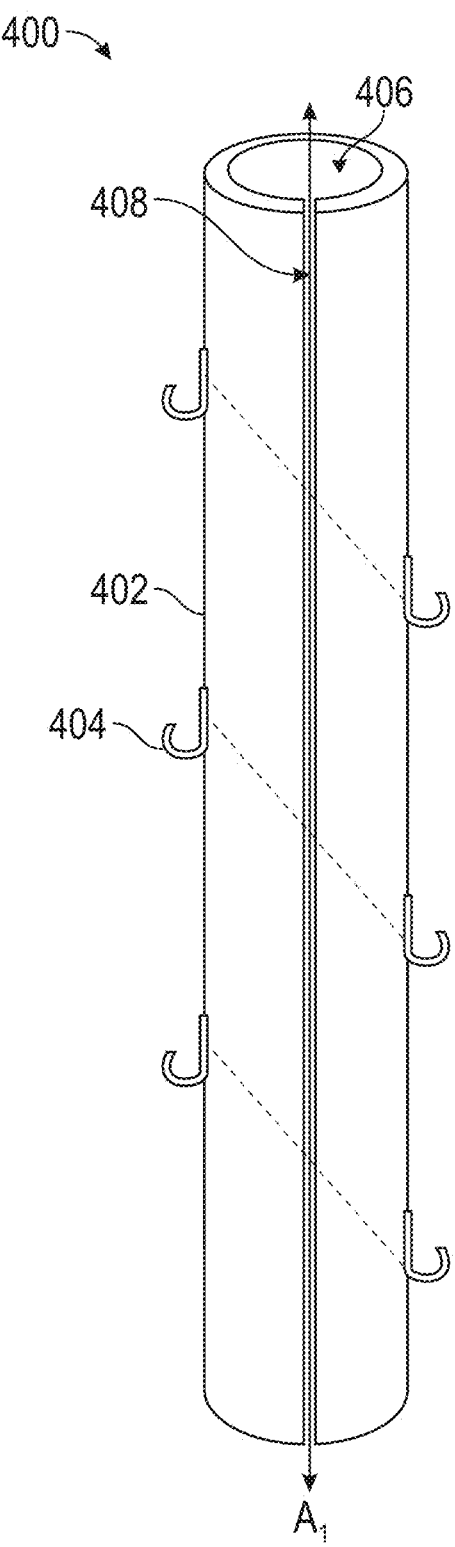

FIGS. 4A-4D illustrate an organizer 400 with a spiral holder configuration, in accordance with embodiments of the present technology. Specifically, FIG. 4A is a front perspective view of the organizer 400, FIG. 4B is a rear perspective view of the organizer 400, and FIGS. 4C and 4D are top views of the organizer 400 showing different circumferential holder positions.

The organizer 400 can be generally similar to the organizers discussed herein, such as the organizer 200 of FIG. 2. For instance, the organizer 400 can be configured to be removably coupled to a support device (e.g., an IV pole) to support medical tubing and/or wiring from one or more medical devices in a patient environment. The organizer 400 can include a tubular member 402 and a plurality of holders 404 coupled to the tubular member 402. The tubular member 402 can further include a lumen 406 along a longitudinal axis $A_1$. In some embodiments, the tubular member 402 further includes a longitudinal slit 408, and the tubular member 402 is separable at the longitudinal slit 408 for removal from and/or insertion on the support device.

In some embodiments, the plurality of holders 404 are arranged around the tubular member 402 to improve organization of the tubing and/or wiring. For instance, the holders 404 can be distributed at different vertical and/or circumferential positions on the tubular member 402 to provide multiple locations for securing the tubing and/or wiring. In some embodiments, the plurality of holders 404 are arranged in a spiral configuration around the longitudinal axis $A_1$ along the length of the tubular member 402. Specifically, the holders 404 can be at different vertical positions along the longitudinal axis $A_1$ (e.g., as shown in FIGS. 4A and 4B) and also at different circumferential positions (e.g., as shown by holders 404a-404g in in FIGS. 4C and 4D), such that the holders 404 are arranged along a spiral trajectory on the tubular member 402 (e.g., as indicated by broken lines in FIGS. 4A and 4B). For example, referring to FIG. 4C, a plurality of holders 404a-404d can be separated circumferentially from each other by an angle $\theta_1$, where the angle $\theta_1$ is or is approximately 90°. As another example, referring to FIG. 4D, a plurality of holders 404e-404g can be separated circumferentially from each other by an angle $\theta_2$ that is or is approximately 120°. Other angles are also possible, e.g., an angle within a range from 5° to 15°, 15° to 25°, 25° to 50°, 50° to 90°, 90° to 180°, etc.

The spiral configuration of the holders 404 depicted in FIGS. 4A-4D can advantageously improve the number of contact points between the organizer 400 and the tubing and/or wiring while maintaining a small number of holders 404. For instance, rather than being continuously supported around the tubular member 402, the tubing and/or wiring can be draped from one holder 404 to another around the tubular member 402. Moreover, longer tubes and/or wires can be accommodated by the organizer 400 via the spiral configuration.

Alternatively or in combination, the holders 404 can be arranged in a variety of configurations besides a spiral configuration. For instance, the holders 404 may be arranged in a linear configuration, circular configuration, square wave configuration, a triangle wave configuration, a sine wave configuration, a sawtooth wave configuration, a staircase configuration, and/or other suitable configurations around the tubular member 402 along the longitudinal axis $A_1$. In any of these configurations, some or all of the holders 404 can be at the same vertical position but at different circumferential positions, some or all of the holders 404 can be at the same circumferential position but at different vertical positions, and/or some or all of the holders 404 can be at different vertical positions and different circumferential positions. Moreover, not all configurations will span the entire external surface area of the tubular member. For instance, the holders 404 may be arranged only on a frontal region of the tubular member 402 (e.g., opposite the longitudinal slit 408), only on a posterior region of the tubular member 402 (e.g., adjacent the longitudinal slit 408), only on an upper region of the tubular member 402, only on an intermediate region of the tubular member 402, or only on a lower region of the tubular member 402, or elsewhere on the tubular member 402.

Figure 5C:
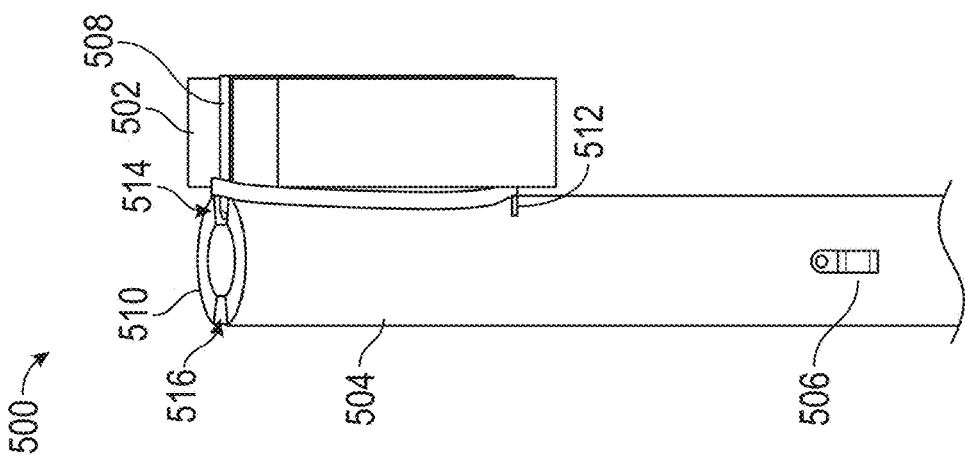
FIGS. 5A-5C illustrate an organizer configured to receive a medical device, in accordance with embodiments of the present technology.
Figure 5B:
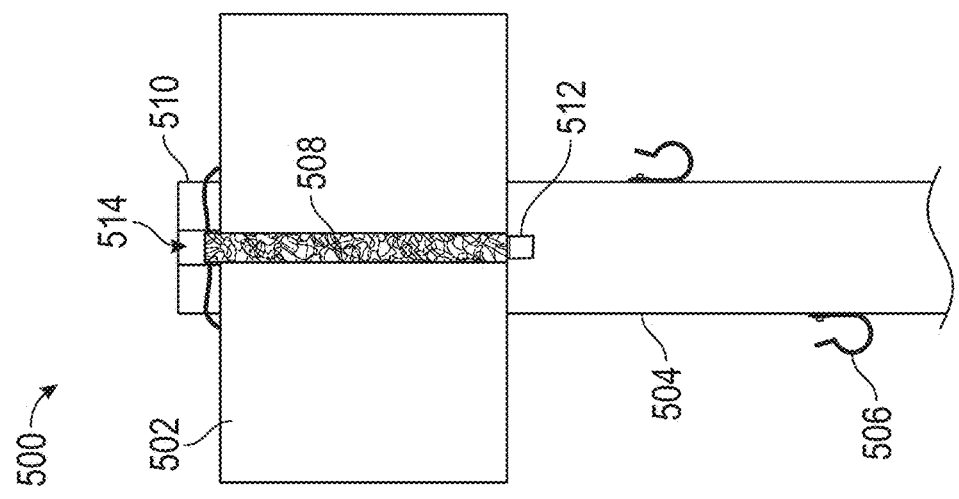
Figure 5A:
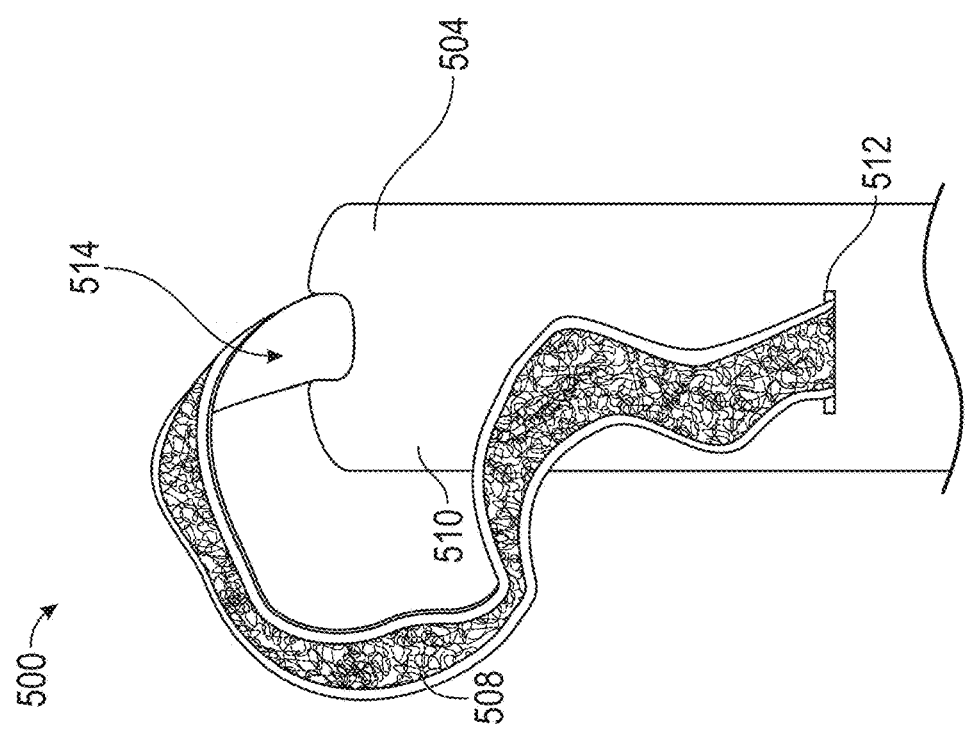

FIGS. 5A-5C illustrate an organizer 500 configured to support medical tubing and/or wiring and one or more medical devices 502, in accordance with embodiments of the present technology. Specifically, FIG. 5A is a front view of the organizer 500, FIG. 5B is a front view of the organizer 500 with a coupled medical device 502, and FIG. 5C is a perspective side view of the organizer 500 with the coupled medical device 502. Referring to FIGS. 5A-5C collectively, the organizer 500 can be generally similar to the organizers provided herein, such as the organizer 200 of FIGS. 2A-2E and/or the organizer 400 of FIGS. 4A-4D. For instance, the organizer 500 can include a tubular member 504 and a plurality of holders 506 coupled to the tubular member 504 for supporting medical tubing and/or wiring from one or more medical devices in a patient environment.

The organizer 500 can be coupled to at least one medical device 502 (shown schematically in FIGS. 5B and 5C), such as one or more IV pumps, displays, diagnostic equipment, sensing equipment (e.g., pulse oximeters, patient monitors), therapeutic equipment (e.g., dialysis machines), electronic communication devices, etc. In some embodiments, the organizer 500 includes one or more attachment features for facilitating coupling of the medical device 502 to the tubular member 504. For instance, the organizer 500 can include a strap 508 configured to wrap around at least a portion of the medical device 502 to secure the medical device 502 to the tubular member 504. The strap 508 can be a hook and loop strap, adjustable cable strap, and/or a cinch strap, for example. The strap 508 can be attached to an upper end 510 of the tubular member 504 so that the medical device 502 does not obstruct the holders 506 along the tubular member 504, and so that any tubing and/or wiring from the medical device 502 (not shown) can be supported in the holders 506.

In the illustrated embodiment, the upper end 510 of the tubular member 504 includes a slot 512 configured to accommodate a portion of the strap 508 to couple the strap 508 to the tubular member 504. Specifically, the strap 508 can be arranged in a loop that passes through the slot 512 and over the upper end 510 of the tubular member 504. The medical device 502 can be placed within the loop and the strap 508 can be tightened around the medical device 502 (e.g., via a buckle on the strap 508 and/or by tying the strap 508 around the medical device 502), thereby securing the medical device 502 to the tubular member 504.

Optionally, the upper end 510 of the tubular member 504 can include a notch 514 formed therein to accommodate the strap 508 and/or to allow the strap 508 to be tightened around the medical device 502. In some embodiments, the notch 514 is positioned opposite a longitudinal slit 516 of the tubular member 504 (FIG. 5C). In some embodiments, the strap 508 extends through the notch 514 but does not extend over the longitudinal slit 516. In other embodiments, the notch 514 can be positioned elsewhere in the upper end 510 of the tubular member 504, such as adjacent to the longitudinal slit 516.

Figure 6:
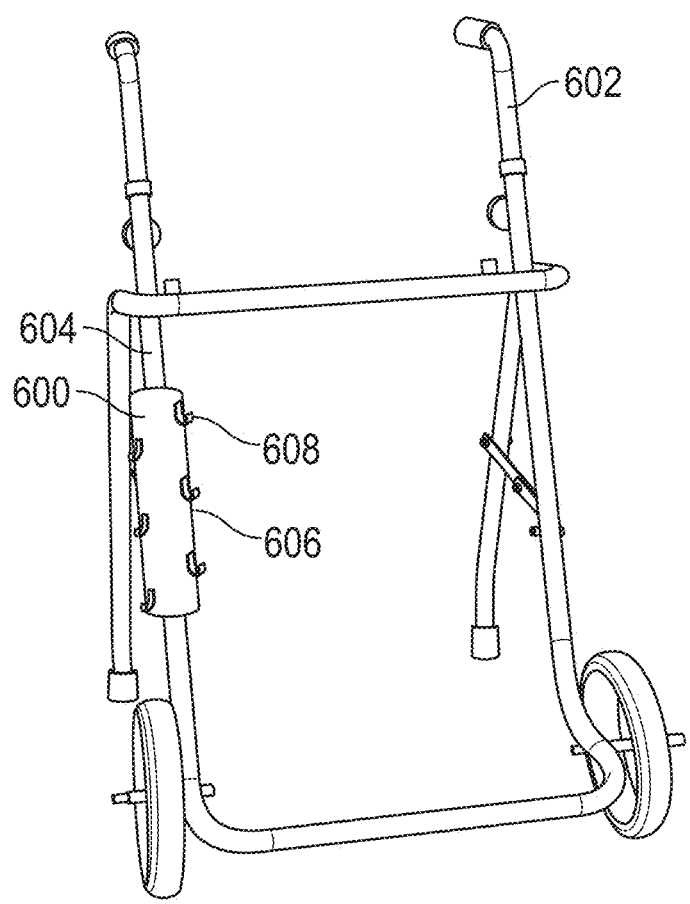
FIG. 6 is a perspective view of an organizer on a medical walker, in accordance with embodiments of the present technology.

FIG. 6 is a perspective view of an organizer 600 positioned on a medical walker 602, in accordance with embodiments of the present technology. The organizer 600 can be the same or substantially similar to any of the organizers disclosed herein (e.g., the organizer 200 of FIGS. 2A-2E, the organizer 400 of FIGS. 4A-4D, and/or the organizer 500 of FIGS. 5A-5C). For instance, the organizer 600 can include a tubular member 606 and a plurality of holders 608 configured to support medical tubing and/or wiring from one or more medical devices in the patient environment (not shown). In the illustrated embodiment, the organizer 600 is coupled to a substantially vertical section 604 of the walker 602, such as to a leg of the walker 602. The organizer 600 can thus be used to support tubing and/or wiring from one or more medical devices on or proximate to the walker 602 (e.g., an IV bag, IV pump, patient monitor, etc., supported by the IV pole). Accordingly, a patient can use the walker 602 while remaining connected to the medical device with reduced risk of entanglement and tripping by the tubing and/or wiring, and also while keeping the tubing and/or wiring suspended above the ground to avoid contamination.

Figure 7:
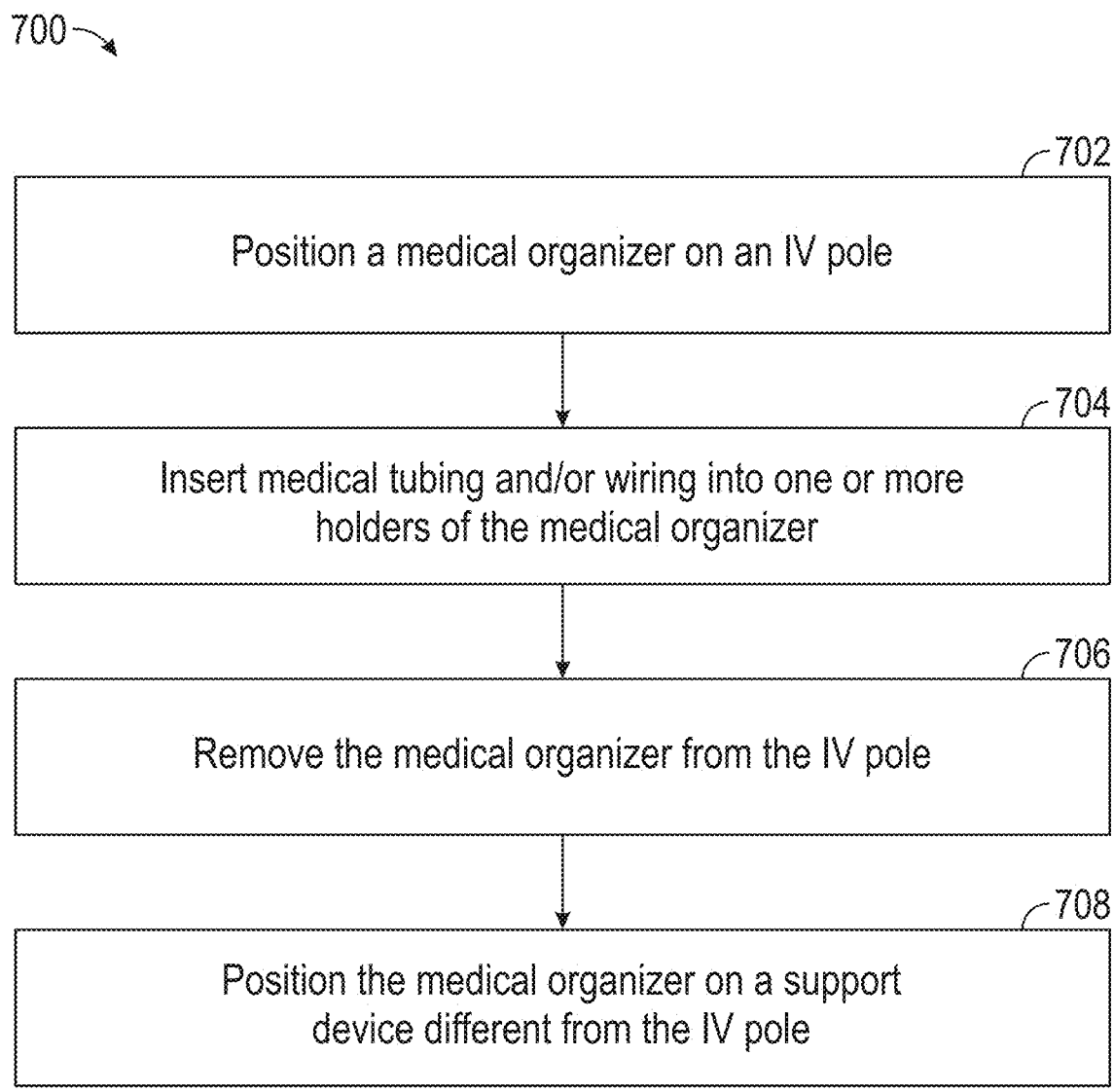
FIG. 7 is a flow diagram illustrating a method for repositioning and positioning an organizer in a patient environment, in accordance with embodiments of the present technology.

FIG. 7 is a flow diagram illustrating a method 700 for repositioning and positioning an organizer in a patient environment, in accordance with embodiments of the present technology. The method 700 can be used to support medical tubing and/or wiring in the patient environment via an organizer. The method 700 can be performed using any of the devices described herein, such as any of the embodiments of FIGS. 2A-6.

The method 700 can begin at block 702 with positioning a medical organizer on an IV pole. For example, the medical organizer can include a tubular member having a lumen and a longitudinal slit connected to the lumen. To position the medical organizer on the IV pole, the tubular member can be separated at the longitudinal slit to insert the IV pole into the lumen via the longitudinal slit. In some embodiments, the tubular member is made from an elastic material (e.g., a polymeric foam) such that the tubular member applies compressive forces to the IV pole to keep the tubular member in place on the IV pole.

The method 700 can continue at block 704 with inserting medical tubing and/or wiring into one or more holders of the medical organizer. The medical tubing and/or wiring can be connected to one or more medical devices (e.g., IV bags, IV pumps, displays, diagnostic equipment, sensing equipment, therapeutic equipment, electronic communication devices) that are carried by and/or proximate to the IV pole. The holders can be hooks, clasps, clips, or other fasteners that are coupled to the tubular member for supporting and organizing the medical tubing and/or wiring. For example, some or all of the holders can be curved hooks having a first end coupled to the tubular member, a second end that is not coupled to the tubular member, and a receiving region extending between the first end and the second end. The first end and the second end can be separated by a gap to allow the medical tubing and/or wiring to be inserted into and removed from the receiving region via the gap.

The method 700 can continue at block 706 with removing the medical organizer from the IV pole, and then at block 708 with positioning the medical organizer on a support device different from the IV pole. For instance, the support device can be a walker, wheelchair, chair, bed, shower accessory, etc. In some situations, a patient may be transferred to another location without the IV pole, but it may be desirable for the patient to remain connected to at least some of the medical devices on the IV pole during and/or after the transfer. Accordingly, to keep the medical tubing and/or wiring organized during the transfer and/or once the patient is at the other location, the medical organizer can be removed from the IV pole and coupled to another support device. In some embodiments, the medical tubing and/or wiring remains within the holders of the medical organizer while the medical organizer is removed from the IV pole and coupled to the other support device. Alternatively, the medical tubing and/or wiring can be removed from the holders before the medical organizer is coupled to the other support device (e.g., before or after removing the medical organizer from the IV pole), and then reinserted into the holders once the medical organizer is coupled to the other support device. Moreover, once the patient is at the other location, it may be desirable to couple the patient to other medical devices (e.g., additional medical devices on or proximate to the support device). In such cases, the method 700 can further include inserting the medical tubing and/or wiring from the other medical devices into the holders of the medical organizer.

EXAMPLES

The following examples are included to further describe some aspects of the present technology, and should not be used to limit the scope of the technology.

Example 1. An organizer for supporting medical tubing or wiring, the organizer comprising:
- a tubular member configured to be removably coupled to an intravenous (IV) pole in a vertical orientation, the tubular member comprising:
  - a longitudinal axis,
  - a lumen extending along the longitudinal axis, and
  - a longitudinal slit connected to the lumen,
  - wherein the tubular member is configured to separate at the longitudinal slit to insert and remove the IV pole from the lumen; and
- a plurality of holders coupled to the tubular member, wherein each of the holders comprises:
  - a first end pivotally coupled to the tubular member,
  - a second end opposite the first end, and
  - a curved receiving region between the first end and the second end,
  - wherein the curved receiving region is configured to support tubing or wiring of a medical device coupled to the IV pole, and
  - wherein the first end and the second end are separated by a gap for inserting and removing the tubing or wiring from the curved receiving region, and
  - wherein the gap is vertically above the curved receiving region when the tubular member is coupled to the IV pole in the vertical orientation.

Example 2. The organizer of Example 1, wherein the plurality of holders are arranged in a spiral configuration around the longitudinal axis along a length of the tubular member.

Example 3. The organizer of Example 1 or 2, wherein the plurality of holders comprise:
- a first holder at a first circumferential position on the tubular member, and
- a second holder at a second circumferential position on the tubular member opposite the first circumferential position.

Example 4. The organizer of Example 3, wherein the first holder is at a first vertical location on the tubular member, and the second holder is at a second vertical location on the tubular member different from the first vertical location.

Example 5. The organizer of any one of Examples 1 to 4, wherein the tubular member is configured to apply compressive forces to the IV pole to retain the organizer in a first vertical position on the IV pole.

Example 6. The organizer of Example 5, wherein the tubular member is configured to be moved to a second vertical position on the IV pole, and wherein the compressive forces retain the organizer in the second vertical position.

Example 7. The organizer of Example 6, wherein the tubular member is configured to be slidably moved from the first vertical position to the second vertical position.

Example 8. The organizer of any one of Examples 5 to 7, wherein the tubular member is configured to be reoriented on the IV pole by rotating the tubular member around the IV pole while maintaining the first vertical position.

Example 9. The organizer of any one of Examples 1 to 8, wherein the tubular member comprises a foam material.

Example 10. The organizer of any one of Examples 1 to 9, wherein the tubular member comprises an antimicrobial material.

Example 11. The organizer of any one of Examples 1 to 10, wherein the holders are each pivotably coupled to the tubular member via a fastener.

Example 12. The organizer of any one of Examples 1 to 11, wherein the tubular member further comprises one or more slots positioned on an upper end of the tubular member, the one or more slots configured accommodate a strap for securing a second medical device to the tubular member.

Example 13. The organizer of Example 12, wherein the organizer further comprises the strap and the strap is coupled to the tubular member via the one or more slots.

Example 14. The organizer of any one of Examples 1 to 13, wherein the tubular member is further configured to be removably coupled to a mobility device in the vertical orientation.

Example 15. The organizer of Example 14, wherein the mobility device comprises a walker.

Example 16. A method for supporting medical tubing or wiring, the method comprising:
- positioning a medical organizer on an intravenous (IV) pole in a vertical orientation, wherein the medical organizer comprises:
  - a tubular member comprising:
    - a longitudinal axis,
    - a lumen extending along the longitudinal axis, and
    - a longitudinal slit connected to the lumen,
    - wherein the IV pole is inserted into the lumen of the tubular member via the longitudinal slit; and
  - a plurality of holders coupled to the tubular member, wherein each of the holders comprises:
    - a first end that is pivotally coupled to the tubular member,
    - a second end opposite the first end, and
    - a curved receiving region between the first end and the second end,
    - wherein the first end and the second end are separated by a gap that is vertically above the curved receiving region when the tubular member is coupled to the IV pole in the vertical orientation;
- inserting medical tubing or wiring from a medical device coupled to the IV pole through the gap and into the curved receiving region of one or more of the holders;
- removing the medical organizer from the IV pole via the longitudinal slit in the tubular member; and positioning the medical organizer in the vertical orientation on a support device different from the IV pole.

Example 17. The method of Example 16, wherein the IV pole is a first IV pole, and the support device is a second IV pole.

Example 18. The method of Example 16 or 17, wherein the support device comprises a walker.

Example 19. The method of any one of Examples 16 to 18, wherein the plurality of holders are arranged in a spiral configuration around the longitudinal axis along a length of the tubular member.

Example 20. The method of any one of Examples 16 to 19, wherein the plurality of holders comprise:
 a first holder at a first circumferential position on the tubular member, and
 a second holder at a second circumferential position on the tubular member opposite the first circumferential position.

Example 21. The method of Example 20, wherein the first holder is at a first vertical location on the tubular member, and the second holder is a second vertical location on the tubular member different from the first vertical location.

Example 22. The method of any one of Examples 16 to 21, wherein the tubular member is configured to apply compressive forces to the IV pole or the support device to retain the medical organizer in a first vertical position on the IV pole or the support device.

Example 23. The method of Example 22, further comprising moving the tubular member from the first vertical position to a second vertical position on the IV pole or the support device, wherein the compressive forces retain the medical organizer in the second vertical position.

Example 24. The method of Example 23, wherein moving the tubular member from the first vertical position to the second vertical position comprises sliding the tubular member along the IV pole or the support device.

Example 25. The method of any one of Examples 22 to 24, further comprising reorienting the tubular member on the IV pole or the support device by rotating the tubular member while maintaining the first vertical position.

Example 26. The method of any one of Examples 16 to 25, wherein the tubular member comprises a foam material.

Example 27. The method of any one of Examples 16 to 26, wherein the tubular member comprises an antimicrobial material.

Example 28. The method of any one of Examples 16 to 27, wherein the holders are each pivotably coupled to the tubular member via a fastener.

Example 29. The method of any one of Examples 16 to 28, wherein the tubular member further comprises one or more slots positioned on an upper end of the tubular member, and wherein the method further comprises securing a second medical device to the tubular member using a strap accommodated by the one or more slots.

Example 30. The method of Example 29, wherein the medical organizer further comprises the strap and the strap is coupled to the tubular member via the one or more slots.

CONCLUSION

Although many of the embodiments are described above with respect to systems, devices, and methods for organizing medical tubing and/or wiring, the technology is applicable to other applications and/or other approaches, such as organization of tubing and/or wiring in non-medical contexts (e.g., in industrial or commercial facilities, within the home, etc.). Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1-7.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

As used herein, the terms "generally," "substantially," "about," and similar terms are used as terms of approximation and not as terms of degree, and are intended to account for the inherent variations in measured or calculated values that would be recognized by those of ordinary skill in the art.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded.

It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

What is claimed is:

1. An organizer for supporting medical tubing or wiring, the organizer comprising:
 a tubular member configured to be removably coupled to an intravenous (IV) pole in a vertical orientation, the tubular member comprising:
  a longitudinal axis,
  a lumen extending along the longitudinal axis,
  a longitudinal slit connected to the lumen,
  a notch formed in an upper end of the tubular member,
  a slot formed in the tubular member below the notch, and
  a strap extending through the notch and the slot to form a loop configured to receive a first medical device, wherein the strap is configured to secure the first medical device to the tubular member, wherein the tubular member is configured to separate at the longitudinal slit to insert and remove the IV pole from the lumen, and wherein the tubular member comprises an elastic polymeric foam, the elastic polymeric foam configured to exert compressive forces against the IV pole to retain the organizer in the vertical orientation without a fastener; and a plurality of holders coupled to the tubular member, wherein each of the holders comprises:
 a first end pivotally coupled to the tubular member,
 a second end opposite the first end, and
 a curved receiving region between the first end and the second end,
 wherein the curved receiving region is configured to support tubing or wiring of a second medical device coupled to the IV pole,
 wherein the first end and the second end are separated by a gap for inserting and removing the tubing or wiring from the curved receiving region, and
 wherein the gap is vertically above the curved receiving region when the tubular member is coupled to the IV pole in the vertical orientation.

2. The organizer of claim 1, wherein the plurality of holders are arranged in a spiral configuration around the longitudinal axis along a length of the tubular member.

3. The organizer of claim 1, wherein the plurality of holders comprise:
 a first holder at a first circumferential position on the tubular member, and
 a second holder at a second circumferential position on the tubular member opposite the first circumferential position.

4. The organizer of claim 3, wherein the first holder is at a first vertical location on the tubular member, and the second holder is at a second vertical location on the tubular member different from the first vertical location.

5. The organizer of claim 1, wherein the tubular member is at a first vertical position on the IV pole, and wherein the compressive forces retain the organizer in the first vertical position.

6. The organizer of claim 5, wherein the tubular member is configured to be moved to a second vertical position on the IV pole, and wherein the compressive forces retain the organizer in the second vertical position.

7. The organizer of claim 6, wherein the tubular member is configured to be slidably moved from the first vertical position to the second vertical position.

8. The organizer of claim 5, wherein the tubular member is configured to be reoriented on the IV pole by rotating the tubular member around the IV pole while maintaining the first vertical position.

9. The organizer of claim 1, wherein the tubular member comprises an antimicrobial material.

10. The organizer of claim 1, wherein the holders are each pivotally coupled to the tubular member via a fastener.

11. The organizer of claim 1, wherein the notch is positioned opposite the longitudinal slit.

12. The organizer of claim 1, wherein the tubular member is further configured to be removably coupled to a mobility device in the vertical orientation.

13. The organizer of claim 12, wherein the mobility device comprises a walker.

14. A method for supporting medical tubing or wiring, the method comprising:

positioning a medical organizer on an intravenous (IV) pole in a vertical orientation, wherein the medical organizer comprises:
 a tubular member comprising:
  a longitudinal axis,
  a lumen extending along the longitudinal axis,
  a longitudinal slit connected to the lumen,
  a notch formed in an upper end of the tubular member,
  a slot formed in the tubular member below the notch, and
  a strap extending through the notch and the slot to form a loop,
  wherein the IV pole is inserted into the lumen of the tubular member via the longitudinal slit, and
  wherein the tubular member comprises an elastic polymeric foam, the elastic polymeric foam configured to exert compressive forces against the IV pole to retain the organizer in the vertical orientation without a fastener; and
 a plurality of holders coupled to the tubular member, wherein each of the holders comprises:
  a first end that is pivotally coupled to the tubular member,
  a second end opposite the first end, and
  a curved receiving region between the first end and the second end,
  wherein the first end and the second end are separated by a gap that is vertically above the curved receiving region when the tubular member is coupled to the IV pole in the vertical orientation;
securing a first medical device to the medical organizer by inserting the first medical device into the loop formed by the strap;
inserting medical tubing or wiring from a second medical device coupled to the IV pole through the gap and into the curved receiving region of one or more of the holders;
removing the medical organizer from the IV pole via the longitudinal slit in the tubular member while the medical tubing or wiring is retained within the one or more holders; and
positioning the medical organizer in the vertical orientation on a support device different from the IV pole while the medical tubing or wiring is retained within the one or more holders.

15. The method of claim 14, wherein the IV pole is a first IV pole, and the support device is a second IV pole.

16. The method of claim 14, wherein the support device comprises a walker.

17. The method of claim 14, wherein the plurality of holders are arranged in a spiral configuration around the longitudinal axis along a length of the tubular member.

18. The method of claim 14, wherein the plurality of holders comprise:
 a first holder at a first circumferential position on the tubular member, and
 a second holder at a second circumferential position on the tubular member opposite the first circumferential position.

19. The method of claim 18, wherein the first holder is at a first vertical location on the tubular member, and the second holder is a second vertical location on the tubular member different from the first vertical location.

20. The method of claim 14, wherein the tubular member is in a first vertical position on the IV pole or the support device, and wherein the compressive forces retain the medical organizer in the first vertical position.

21. The method of claim 20, further comprising moving the tubular member from the first vertical position to a second vertical position on the IV pole or the support device, wherein the compressive forces retain the medical organizer in the second vertical position.

22. The method of claim 21, wherein moving the tubular member from the first vertical position to the second vertical position comprises sliding the tubular member along the IV pole or the support device.

23. The method of claim 20, further comprising reorienting the tubular member on the IV pole or the support device by rotating the tubular member while maintaining the first vertical position.

24. The method of claim 14, wherein the tubular member comprises an antimicrobial material.

25. The method of claim 14, wherein the holders are each pivotally coupled to the tubular member via a fastener.

26. The method of claim 14, wherein the notch is positioned opposite the longitudinal slit.

27. The organizer of claim 1, wherein the gap spans a length within a range from 5 mm to 15 mm.

28. The organizer of claim 1, wherein the curved receiving region has an arc angle of greater than or equal to 270 degrees.

29. The organizer of claim 1, wherein the lumen of the tubular member has a first diameter when the tubular member is in a resting configuration, and the lumen has a second diameter greater than the first diameter when the tubular member is coupled to the IV pole.

30. The method of claim 14, wherein positioning the medical organizer on the IV pole comprises stretching the tubular member so that an inner diameter of the tubular member is enlarged to match or exceed an outer diameter of the IV pole.

* * * * *